(12) United States Patent
Syed

(10) Patent No.: US 10,588,766 B2
(45) Date of Patent: Mar. 17, 2020

(54) STEERABLE INTRAVASCULAR ANCHOR AND METHOD OF OPERATION

(71) Applicant: RAM MEDICAL INNOVATIONS, LLC, Springfield, OH (US)

(72) Inventor: Mubin I. Syed, Springfield, OH (US)

(73) Assignee: RAM MEDICAL INNOVATIONS, LLC, Springfield, OH (US)

( * ) Notice: Subject to any disclaimer, the term of this patent is extended or adjusted under 35 U.S.C. 154(b) by 687 days.

(21) Appl. No.: 14/638,438

(22) Filed: Mar. 4, 2015

(65) Prior Publication Data

US 2015/0174377 A1  Jun. 25, 2015

Related U.S. Application Data

(63) Continuation-in-part of application No. PCT/US2013/071271, filed on Nov. 21, 2013.
(Continued)

(51) Int. Cl.
*A61F 2/95* (2013.01)
*A61M 25/04* (2006.01)
*A61M 25/09* (2006.01)

(52) U.S. Cl.
CPC .............. *A61F 2/95* (2013.01); *A61M 25/04* (2013.01); *A61M 25/09* (2013.01);
(Continued)

(58) Field of Classification Search
CPC .................. A61M 25/04; A61M 25/09; A61M 2025/09125; A61M 2025/09175; A61M 2025/09183; A61F 2/95
See application file for complete search history.

(56) References Cited

U.S. PATENT DOCUMENTS 4,243,040 A  1/1981 Beecher
4,790,331 A  12/1988 Okada et al.
(Continued)

FOREIGN PATENT DOCUMENTS

CN  108472124 A  8/2018
CN  108472472 A  8/2018
(Continued)

OTHER PUBLICATIONS

Godwin, J., The Circulatory and Respiratory Systems, Z0250 Lab III, 2002, retrieved from: https://projects.ncsu.edu/cals/course/zo250/lab-3.html.
(Continued)

*Primary Examiner* — Devin B Henson
(74) *Attorney, Agent, or Firm* — Jennifer Hayes; Nixon Peabody LLP

(57) ABSTRACT

A steerable intravascular anchor comprises an anchor portion that is steerable to a position and then pinned thereto by an external device protruding through the superficial temporal artery. The pin is steered through the skin into the anchor under, for example, by fluoroscopic guidance. The anchor portion, in one embodiment, may have a figure-eight shape, and that comprises two wires, each wire forming a ring. The rings may be located in the same plane or at an angle with respect to one other. Alternatively, the anchor portion comprises a plurality of wires, each wire forming a ring, each ring being connected to at least one other ring. It will be appreciated that other wire shapes may be used, including loops, triangles, squares, pentagons, hexagons, and the like, and combinations thereof.

17 Claims, 11 Drawing Sheets

Related U.S. Application Data

(60) Provisional application No. 61/728,862, filed on Nov. 21, 2012.

(52) U.S. Cl.
CPC ............ *A61M 2025/09125* (2013.01); *A61M 2025/09175* (2013.01); *A61M 2025/09183* (2013.01); *A61M 2205/0266* (2013.01)

(56) References Cited

U.S. PATENT DOCUMENTS

| | | | |
|---|---|---|---|
| 5,098,707 A | 3/1992 | Baldwin et al. | |
| 5,293,772 A | 9/1994 | Carr, Jr. | |
| 5,344,426 A | 9/1994 | Lau et al. | |
| 5,419,777 A | 5/1995 | Hofling | |
| 5,571,135 A | 11/1996 | Fraser et al. | |
| 5,651,366 A | 7/1997 | Liang et al. | |
| 5,662,703 A | 9/1997 | Yurek et al. | |
| 5,669,924 A | 9/1997 | Shaknovich | |
| 5,690,644 A | 11/1997 | Yurek et al. | |
| 5,718,702 A | 2/1998 | Edwards | |
| 5,720,735 A | 2/1998 | Dorros | |
| 5,766,192 A | 6/1998 | Zacca | |
| 5,807,330 A | 9/1998 | Teitelbaum | |
| 5,813,976 A * | 9/1998 | Filipi .................. | A61B 1/0055 600/102 |
| 5,957,901 A | 9/1999 | Mottola et al. | |
| 5,997,563 A | 12/1999 | Kretzers | |
| 6,027,462 A | 2/2000 | Greene et al. | |
| 6,059,813 A | 5/2000 | Vrba et al. | |
| 6,070,589 A | 6/2000 | Keith et al. | |
| 6,152,141 A | 11/2000 | Stevens et al. | |
| 6,238,410 B1 | 5/2001 | Vrba et al. | |
| 6,245,017 B1 | 6/2001 | Hashimoto | |
| 6,245,573 B1 | 6/2001 | Spillert | |
| 6,428,567 B2 | 8/2002 | Wilson et al. | |
| 6,450,964 B1 | 9/2002 | Webler | |
| 6,464,665 B1 * | 10/2002 | Heuser .................. | A61B 17/11 604/101.01 |
| 6,494,875 B1 | 12/2002 | Mauch | |
| 6,544,278 B2 | 4/2003 | Vrba et al. | |
| 6,663,613 B1 | 12/2003 | Lewis et al. | |
| 6,764,505 B1 | 7/2004 | Hossainy et al. | |
| 6,780,174 B2 | 8/2004 | Mauch | |
| 6,808,520 B1 | 10/2004 | Fouirkas et al. | |
| 6,837,881 B1 | 1/2005 | Barbut | |
| 6,929,633 B2 | 8/2005 | Evans et al. | |
| 6,932,829 B2 | 8/2005 | Majercak | |
| 6,942,682 B2 | 9/2005 | Vrba et al. | |
| 7,235,083 B1 | 6/2007 | Perez et al. | |
| 7,393,358 B2 | 7/2008 | Malewicz | |
| 7,651,520 B2 | 1/2010 | Fischell et al. | |
| 7,674,493 B2 | 3/2010 | Hossainy et al. | |
| 7,740,791 B2 | 6/2010 | Kleine et al. | |
| 7,758,624 B2 | 7/2010 | Dorn et al. | |
| 7,763,010 B2 | 7/2010 | Evans et al. | |
| 7,766,961 B2 | 8/2010 | Patel et al. | |
| 7,828,832 B2 | 11/2010 | Belluche et al. | |
| 7,842,026 B2 | 11/2010 | Cahill et al. | |
| 7,955,370 B2 | 6/2011 | Gunderson | |
| 8,092,509 B2 | 1/2012 | Dorn et al. | |
| 8,119,184 B2 | 2/2012 | Hossainy et al. | |
| 8,202,309 B2 | 6/2012 | Styrc | |
| 8,241,241 B2 | 8/2012 | Evans et al. | |
| 8,343,181 B2 | 1/2013 | Duffy et al. | |
| 8,419,767 B2 | 4/2013 | Al-Qbandi et al. | |
| 8,535,290 B2 | 9/2013 | Evans et al. | |
| 8,721,714 B2 | 5/2014 | Kelley | |
| 8,727,988 B2 | 5/2014 | Flaherty et al. | |
| 8,728,144 B2 | 5/2014 | Fearnot | |
| 8,740,971 B2 | 6/2014 | Iannelli | |
| 8,986,241 B2 | 3/2015 | Evans et al. | |
| 8,998,894 B2 | 4/2015 | Mauch et al. | |
| 9,301,830 B2 | 4/2016 | Heuser et al. | |
| 9,314,499 B2 | 4/2016 | Wang et al. | |
| 9,636,244 B2 | 5/2017 | Syed | |
| 9,855,705 B2 | 1/2018 | Wang et al. | |
| 9,980,838 B2 | 5/2018 | Syed | |
| 2001/0003985 A1 | 6/2001 | Lafontaine et al. | |
| 2001/0049534 A1 | 12/2001 | Lachat | |
| 2002/0077691 A1 | 6/2002 | Nachtigall | |
| 2002/0123698 A1 | 9/2002 | Garibotto et al. | |
| 2002/0156518 A1 | 10/2002 | Tehrani | |
| 2002/0165535 A1 | 11/2002 | Lesh | |
| 2003/0088187 A1 | 5/2003 | Saadat et al. | |
| 2003/0216721 A1 | 11/2003 | Diederich | |
| 2003/0229282 A1 | 12/2003 | Burdette | |
| 2004/0073190 A1 | 4/2004 | Deem et al. | |
| 2004/0087995 A1 | 5/2004 | Copa et al. | |
| 2004/0138734 A1 | 7/2004 | Chobotov et al. | |
| 2004/0147837 A1 | 7/2004 | Macaulay et al. | |
| 2004/0167463 A1 | 8/2004 | Zawacki et al. | |
| 2005/0043779 A1 | 2/2005 | Wilson | |
| 2005/0085841 A1 | 4/2005 | Eversull et al. | |
| 2005/0101968 A1 * | 5/2005 | Dadourian ................ | A61F 2/95 606/108 |
| 2005/0113862 A1 | 5/2005 | Besselink et al. | |
| 2005/0222488 A1 | 10/2005 | Chang et al. | |
| 2005/0234499 A1 | 10/2005 | Olson et al. | |
| 2005/0251160 A1 | 11/2005 | Saadat et al. | |
| 2006/0025752 A1 | 2/2006 | Broaddus et al. | |
| 2006/0025844 A1 | 2/2006 | Majercak et al. | |
| 2006/0030923 A1 | 2/2006 | Gunderson | |
| 2006/0036218 A1 | 2/2006 | Goodson et al. | |
| 2006/0155363 A1 | 7/2006 | Laduca et al. | |
| 2006/0200221 A1 | 9/2006 | Malewicz | |
| 2006/0257389 A1 | 11/2006 | Binford | |
| 2006/0259063 A1 * | 11/2006 | Bates .................... | A61M 25/09 606/198 |
| 2006/0270900 A1 | 11/2006 | Chin et al. | |
| 2007/0016019 A1 | 1/2007 | Salgo | |
| 2007/0016062 A1 | 1/2007 | Park | |
| 2007/0038061 A1 | 2/2007 | Huennekens et al. | |
| 2007/0038293 A1 | 2/2007 | St Goar et al. | |
| 2007/0049867 A1 | 3/2007 | Shindelman | |
| 2007/0083215 A1 | 4/2007 | Hamer et al. | |
| 2007/0118151 A1 | 5/2007 | Davidson et al. | |
| 2007/0129719 A1 | 6/2007 | Kendale et al. | |
| 2008/0039746 A1 | 2/2008 | Hissong et al. | |
| 2008/0114239 A1 | 5/2008 | Randall et al. | |
| 2008/0194993 A1 * | 8/2008 | McLaren ............... | A61M 25/09 600/585 |
| 2008/0208309 A1 | 8/2008 | Saeed | |
| 2008/0281398 A1 | 11/2008 | Koss | |
| 2009/0005679 A1 | 1/2009 | Dala-Krishna | |
| 2009/0018526 A1 * | 1/2009 | Power ................... | A61M 25/09 604/508 |
| 2009/0036780 A1 | 2/2009 | Abraham | |
| 2009/0093791 A1 | 4/2009 | Heuser | |
| 2009/0132019 A1 | 5/2009 | Duffy et al. | |
| 2009/0171293 A1 | 7/2009 | Yang et al. | |
| 2009/0177035 A1 | 7/2009 | Chin | |
| 2009/0240253 A1 | 9/2009 | Murray | |
| 2009/0254116 A1 | 10/2009 | Rosenschein et al. | |
| 2009/0270975 A1 | 10/2009 | Giofford, III et al. | |
| 2009/0319017 A1 | 12/2009 | Berez et al. | |
| 2010/0016943 A1 | 1/2010 | Chobotov | |
| 2010/0024818 A1 | 2/2010 | Stenzler et al. | |
| 2010/0030165 A1 | 2/2010 | Takagi et al. | |
| 2010/0030256 A1 | 2/2010 | Dubrul et al. | |
| 2010/0069852 A1 | 3/2010 | Kelley | |
| 2010/0168583 A1 | 7/2010 | Dausch et al. | |
| 2010/0185161 A1 | 7/2010 | Pellegrino et al. | |
| 2010/0185231 A1 | 7/2010 | Lashinski | |
| 2010/0204708 A1 | 8/2010 | Sharma | |
| 2010/0268067 A1 | 10/2010 | Razzaque et al. | |
| 2010/0272740 A1 | 10/2010 | Vertegel et al. | |
| 2010/0298922 A1 | 11/2010 | Thornton et al. | |
| 2011/0009943 A1 | 1/2011 | Paul et al. | |
| 2011/0034987 A1 | 2/2011 | Kennedy | |
| 2011/0071394 A1 | 3/2011 | Fedinec | |
| 2011/0082533 A1 | 4/2011 | Vardi et al. | |
| 2011/0213459 A1 | 9/2011 | Garrison | |

(56) References Cited

U.S. PATENT DOCUMENTS

| | | |
|---|---|---|
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0022636 A1 | 1/2012 | Chobotov |
| 2012/0029478 A1 | 2/2012 | Kurosawa |
| 2012/0034205 A1 | 2/2012 | Alkon |
| 2012/0035590 A1 | 2/2012 | Whiting et al. |
| 2012/0169712 A1 | 7/2012 | Hill et al. |
| 2012/0020942 A1 | 8/2012 | Hall et al. |
| 2012/0209375 A1 | 8/2012 | Madrid et al. |
| 2012/0289945 A1 | 11/2012 | Segermark |
| 2013/0053792 A1 | 2/2013 | Fischell et al. |
| 2013/0131777 A1 | 5/2013 | Hartley et al. |
| 2013/0296773 A1 | 11/2013 | Feng et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0142427 A1 | 5/2014 | Petroff |
| 2014/0214002 A1 | 7/2014 | Thermopeutix |
| 2014/0228808 A1 | 8/2014 | Webster et al. |
| 2014/0358123 A1 | 12/2014 | Ueda et al. |
| 2015/0018942 A1 | 1/2015 | Hung et al. |
| 2015/0190576 A1 | 7/2015 | Lee et al. |
| 2015/0201900 A1 | 7/2015 | Syed |
| 2015/0245933 A1* | 9/2015 | Syed .................... A61M 25/09 623/1.23 |
| 2015/0250991 A1 | 9/2015 | Silvestro |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1 | 5/2016 | Siegel et al. |
| 2016/0296355 A1 | 10/2016 | Syed |
| 2016/0338835 A1 | 11/2016 | Bioventrix |
| 2017/0119562 A1 | 5/2017 | Syed |
| 2017/0119563 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |
| 2018/0042743 A1 | 2/2018 | Syed |
| 2018/0059124 A1 | 3/2018 | Syed |
| 2018/0116780 A1 | 5/2018 | Laine |
| 2018/0250147 A1 | 9/2018 | Syed |
| 2019/0091441 A1 | 3/2019 | Syed |
| 2019/0254675 A1 | 8/2019 | Syed |
| 2019/0255286 A1 | 8/2019 | Syed |
| 2019/0336114 A1 | 11/2019 | Syed |

FOREIGN PATENT DOCUMENTS

| | | |
|---|---|---|
| CN | 108882975 A | 11/2018 |
| CN | 109475722 A1 | 3/2019 |
| EP | 3280355 A1 | 2/2018 |
| EP | 3367969 A1 | 9/2018 |
| EP | 3368123 A1 | 9/2018 |
| EP | 3399944 A1 | 11/2018 |
| EP | 3405261 A1 | 11/2018 |
| IN | 201827018555 A | 10/2018 |
| IN | 201827018768 A | 10/2018 |
| WO | 1996036269 | 11/1996 |
| WO | 2004089249 A1 | 10/2004 |
| WO | 2011/011539 A1 | 1/2011 |
| WO | WO2011/106502 | 9/2011 |
| WO | 2010/129193 A1 | 11/2011 |
| WO | 2011/137336 A1 | 11/2011 |
| WO | 2012030101 | 8/2012 |
| WO | 2014081947 | 5/2014 |
| WO | 2014197839 | 12/2014 |
| WO | 2016164215 | 10/2016 |
| WO | 2017/074492 A1 | 5/2017 |
| WO | 2017/074536 A1 | 5/2017 |
| WO | 2017/127127 A1 | 7/2017 |
| WO | 2017222571 A1 | 12/2017 |
| WO | 2017222612 A1 | 12/2017 |
| WO | 2018/164766 A1 | 9/2018 |
| WO | 2019/070349 A1 | 4/2019 |
| WO | 2019/160625 A1 | 8/2019 |
| WO | 2019/160626 A1 | 8/2019 |

OTHER PUBLICATIONS

Stroke Treatments, American Heart Association, Retrieved from: Http://www.strokeassociation.org/STROKEORG/ AboutStroke/ Treatment/Stroke-Treatments_UCM_310892_Article.jsp#V9Hrg2WfV_1.

Beckman et al., Venous Thromboembolism: A Public Health Concern, Am J Prev Med., 2010, vol. 38(4), pp. S495-S501.

Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.

Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.

International Search Report and Written Opinion for International Application No. PCT/US2016/024795 dated Aug. 30, 2016, 14 pages.

International Search Report and Written Opinion issued for International Application No. PCT/US2016/024794 dated Jul. 1, 2016, 10 pages.

International Search Report and Written Opinion issued for International Application No. PCT/US2016/047163 dated Oct. 28, 2016, 9 pages.

International Search Report and Written Opinion issued for International Application No. PCT/US2017/021188 dated May 10, 2017, 11 pages.

International Preliminary Report on Patentability issued in International Application No. PCT/US2013/071271 dated May 26, 2015, 6 pages.

Office Action issued in U.S. Appl. No. 13/750,920 dated Apr. 8, 2015.

Response to Office Action in U.S. Appl. No. 13/750,920 dated Aug. 10, 2015.

Supplemental Response to Office Action in U.S. Appl. No. 13/750,920 dated Nov. 2, 2015.

Office Action in U.S. Appl. No. 13/750,920 dated Nov. 5, 2015.

Response to Office Action in U.S. Appl. No. 13/750,920 dated Feb. 11, 2016.

International Search Report and Written Opinion issued for International Application No. PCT/US2016/047165 dated Jan. 5, 2017, 13 pages.

International Search Report for PCT/US2013/071271 dated Feb. 10, 2014.

International Preliminary Report on Patentability issued in International Application No. PCT/US2016/024795 dated May 1, 2018, 10 pages.

International Preliminary Report on Patentability issued in International Application No. PCT/US2016/047165 dated May 1, 2018, 5 pages.

International Search Report and Written Opinion issued for PCT/US2018/012834 dated Mar. 15, 2018,13 pages.

Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.

Blaney et al., Alteplase for the Treatment of Central Venous Catheter Occlusion in Children: Results of a Prospective, Open-Label, Single-Arm Study (The Cathflo Activase Pediatric Study), J Vase Interv Radiol, 2006, vol. 17 (11), pp. 1745-1751.

Shah, T., Radiopaque Polymer Formulations for Medical Devices, MDDI Medical Diagnostic and Device Industry: Materials, 2001, retrieved from: https://www.mddionline.com/radiopaque-polymer-formulations-medical-devices.

(56) References Cited

OTHER PUBLICATIONS

International Preliminary Report on Patentability issued for PCT/US2016/047163 dated Dec. 25, 2018, 7 pages.
International Preliminary Report on Patentability issued for PCT/US2017/021188 dated Dec. 25, 2018, 9 pages.
International Search Report and Written Opinion for PCT/US2018/047372 dated Jan. 2, 2019, 8 pages.
International Search Report and Written Opinion for PCT/US2019/012727 dated Mar. 21, 2019, 12 pages.
International Search Report and Written Opinion for PCT/US2019/12745 dated Apr. 1, 2019, 10 pages.
EP 16777055.1 Extended Search Report dated Feb. 12, 2019, 7 pages.
EP 18725097.2 Extended Search Report dated Apr. 24, 2019, 9 pages.
EP 16860437.9 Extended Search Report dated May 17, 2019.
EP 16860409.8 Extended Search Report dated Jun. 27, 2019.

\* cited by examiner

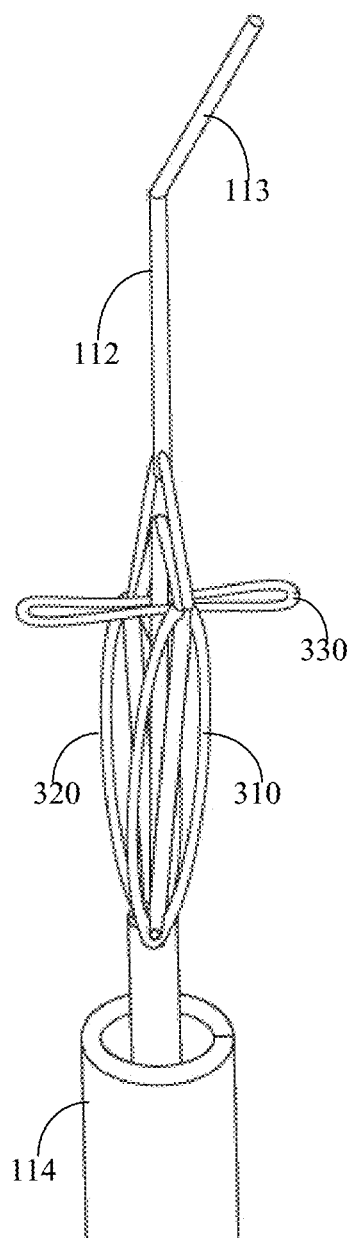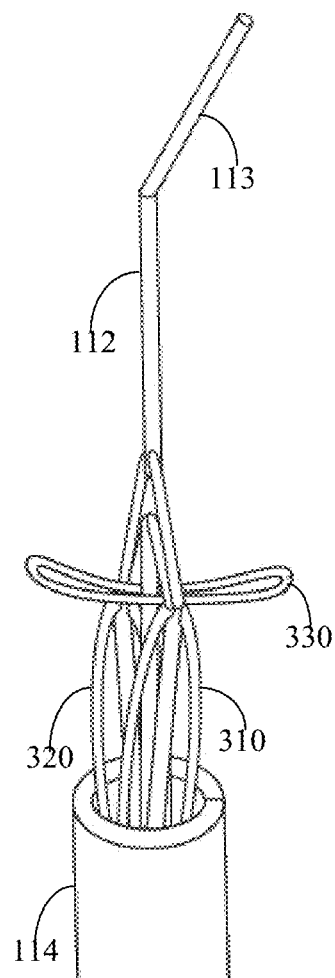
FIGURE 3C
FIGURE 3D

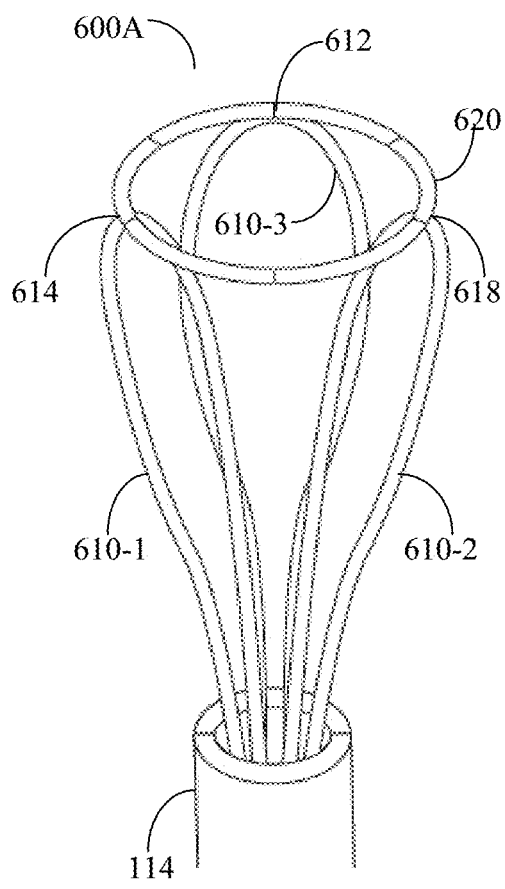
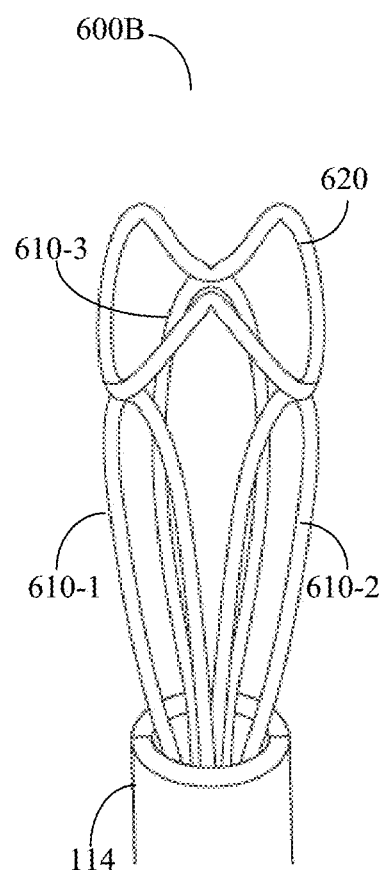
FIGURE 6A
FIGURE 6B

STEERABLE INTRAVASCULAR ANCHOR AND METHOD OF OPERATION

CROSS-REFERENCE TO RELATED APPLICATIONS

This patent application is a continuation-in part application and claims priority to PCT Application No. PCT/US2013/071271, entitled "System for the Intravascular Placement of a Medical Device", and having an international filing date of Nov. 21, 2013, which claims priority to U.S. Provisional Application No. 61/728,862, filed Nov. 21, 2012, both assigned to common assignee, the disclosures of which are herein incorporated by reference in their entirety.

BACKGROUND

1. Field

The invention generally relates to medical devices inserted into bodily arteries and more particularly to the anchoring of a guidewire guided within a bodily artery at a desired position.

2. Related Art

One known medical procedure is the catheterization process. During the catheterization process, a small incision is made in the skin at an entry site. A vascular tube called a sheath is inserted into the artery or vein allowing for easy catheter exchanges during the catheterization procedures. Guided by medical imaging, such as x-rays or other technology, the catheter is then inserted through the skin and maneuvered through the artery. Once the catheter is in place, contrast media may be injected into the blood vessel and an angiogram is taken of the blocked artery to help identify the site of the blockage. With medical imaging, such as x-rays or other technology, guidance, a thin wire called a guidewire may then be moved to the site to guide the placement of a diagnostic catheter, as well as any additional medical devices such as an angioplasty balloon catheter or a vascular stent, as desired.

There are angioplasty procedures that include the placement of a stent, a small, flexible tube made of plastic or wire mesh to support a damaged blood vessel wall. These stents may be self-expandable or balloon expandable, for example. Once the stent is in place, it may remain in the body permanently, acting as a scaffold for the damaged blood vessel. The guidewire, catheter, and any additional medical devices may then be removed from the patient through the entry site.

Technical difficulties in carotid artery stenting have arisen, particularly in the elderly population, due to arch vessel tortusity and aortic arch elongation and distortion. Stenting in this situation has resulted in adverse events, such as dislodgement of the delivery system from the target vessel during the procedure or failure to catheterize with large-caliber sheaths despite numerous attempts. In extreme cases, tears in the carotid artery and aortic arch can result. Also these excessive unsuccessful manipulations can cause plaque embolization from the aortic arch or carotid origin, and can result in a stroke during the procedure. One approach previously used has been obtaining through-and-through guidewire access using a surgical cutdown of the superficial temporal artery to facilitate the carotid artery stenting in these situations. The through-and-through access improves the ability to stabilize and manipulate the guidewire during the procedure and thus facilitates intervention, which may include carotid stenting, intracranial intervention, or other interventional procedures.

Various anchoring systems have been suggested in the prior art ranging from guidewires with releasable barb anchors to the use of expandable baskets, also referred to as a microwhisk, that may be used for the purpose of anchoring the guidewire. What is needed is an improved micro-anchor that can provide superior anchoring capabilities to the known prior art solutions.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

According to some embodiments of the invention, an intravascular system is disclosed that includes a guidewire; and a micro-anchor having a figure eight shape connected to the guidewire, the micro-anchor comprising: a first ring connected to the guidewire; and, a second ring connected to at least one of the first ring and the guidewire.

The first ring may be at an angle relative to the second ring. The intravascular system may further include a third ring, wherein the third ring is connected to at least one of the first ring, second ring and the guidewire.

The first ring and the second ring may each comprise a support extending from one end of the ring to an opposite end of the ring. The support of the first ring may be coaxial with the support of the second ring. The support of the first ring and the support of the second ring may be further coaxial with a longitudinal axis of the guidewire.

The micro-anchor may be capable of accepting a pin, the pin guidable through at least one of the first ring and the second ring to secure the guidewire within an artery.

The guidewire may include a tip, wherein the tip of the guidewire is angled to facilitate selection of an external carotid artery and navigate the guidewire therein. The micro-anchor may be attached to a tip of the guidewire.

The micro-anchor may be moveable between a collapsed first position and an expanded second position. The intravascular system may further include a sheath, the guidewire and the micro-anchor guideable through the sheath. The micro-anchor may be in the collapsed first position while the micro-anchor is within the sheath. The micro-anchor is in the expanded second position while the micro-anchor is outside the sheath.

According to other embodiments of the invention, an intravascular system is disclosed that includes a guidewire; and a micro-anchor connected to the guidewire, the micro-anchor comprising: a plurality of petals connected to the guidewire; and, a ring connected to each of the plurality of petals.

The micro-anchor may be capable of accepting a pin, the pin guidable through at least one of the plurality of petals to secure the guidewire within an artery.

The guidewire may extend through the micro-anchor.

The micro-anchor may be moveable between a collapsed first position and an expanded second position. The intravascular system may further include a sheath, the guidewire and the micro-anchor guideable through the sheath. The micro-anchor may be in the collapsed first position while the micro-anchor is within the sheath. The micro-anchor may be in the expanded second position while the micro-anchor is outside the sheath.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

FIG. 3C is a schematic diagram of the micro-anchor of FIG. 3A in a collapsed position prior to entering into the catheter;

FIG. 3D is a schematic diagram of the micro-anchor of FIG. 3A in a collapsed position partially placed into the catheter;

FIG. 6A is a perspective view of a three-petal micro-anchor according to one embodiment of the invention;

FIG. 6B is a perspective of a the three-petal micro-anchor of FIG. 5A in a collapsed position;

DETAILED DESCRIPTION

A steerable intravascular anchor is disclosed that comprises an anchor portion and is steerable to a position in a superficial temporal artery. The anchor can then be pinned thereto by an external device protruding through the superficial temporal artery by advancing a pin through the skin. The pin is steered through the skin into the anchor under, for example, fluoroscopic guidance. The anchor portion, in one embodiment, may have a figure-eight shape. The anchor portion may include two wires, each wire forming a ring. The rings may be located on the same plane or at an angle relative to one another. In another embodiment, the anchor portion includes a plurality of wires each wire formed in a ring, and each ring being connected to at least one other ring. It will be appreciated that the wires may be formed into other shapes, such as loops, triangles, squares, pentagons, hexagons, and the like, and combinations thereof.

Figure 1:
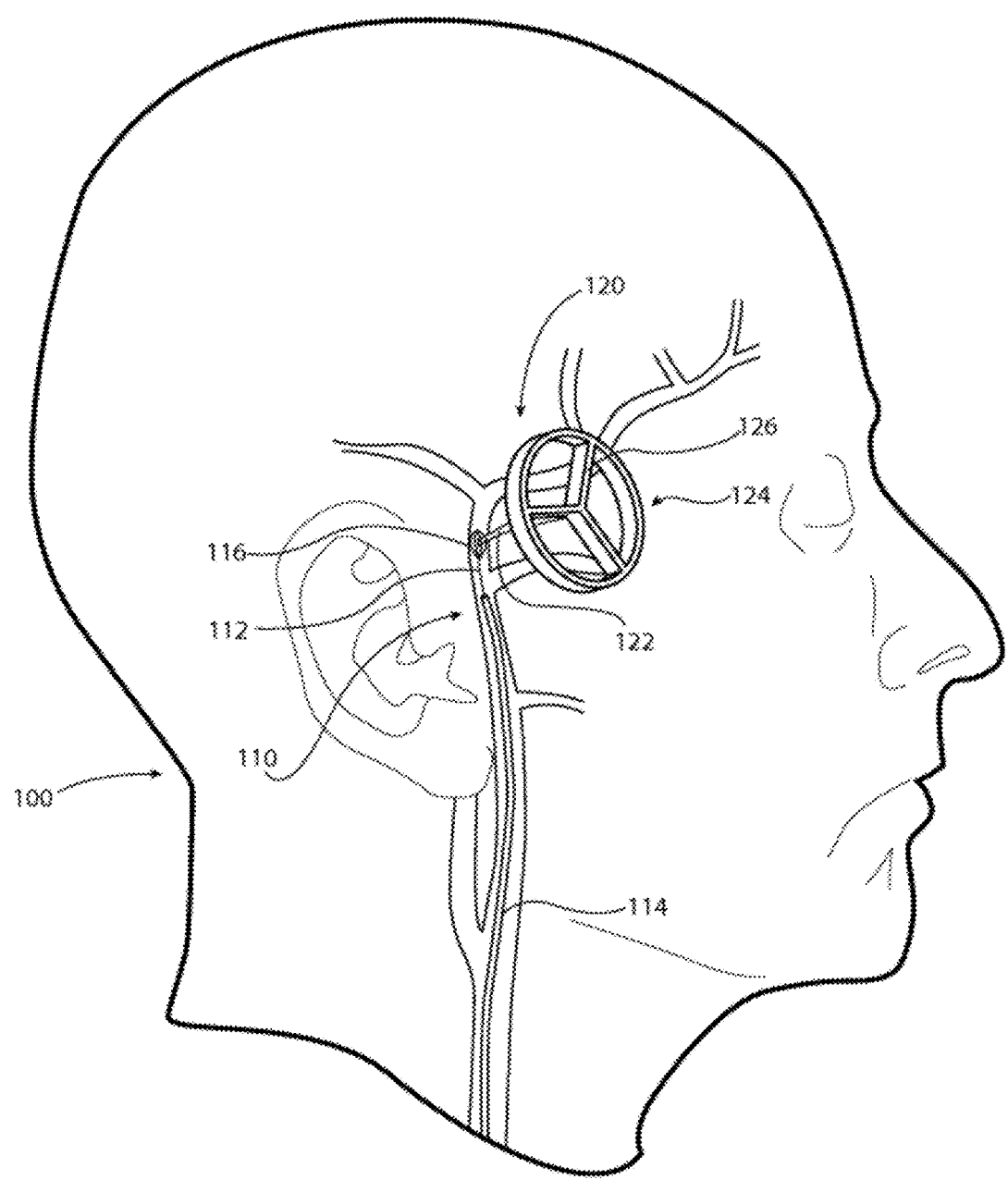
FIG. 1 is a side perspective view of a system for the intravascular placement of a medical device.

FIG. 1 shows an exemplary and non-limiting system for the intravascular placement of a medical device 100. The system 100 has a catheter apparatus component 110 including a guidewire 112 that is surrounded by a guidewire sheath 114. The guidewire sheath 114 is formed from a plastic, for example, a polymer or any other suitable, sterilizable material for a medical device. In some embodiments, the guidewire sheath 114 may be referred to as a micro catheter. The guidewire 112 has a micro-anchor 116 on one end.

The guidewire 112 may be composed of stainless steel which may be monofilament or braided. The guidewire 112 and the micro-anchor 116 may instead be composed of a shape-memory alloy, such as nitinol. Alternatively, the shape-memory alloy may be a copper-aluminum-nickel, or a nickel-titanium, and may be created by alloying zinc, copper, gold and iron. Additionally, the guidewire may be coated in Teflon, polyurethane, or another lubricious polymer.

During one exemplary catheterization process, a small incision is made in the skin at an entry site opening to a blood vessel, for example, the femoral artery. The catheter apparatus component 110, including the guidewire sheath 114 and its enclosed guidewire 112 and micro-anchor 116 (in its collapsed position within the guidewire sheath 114), may then be guided into the blood vessel. The catheter apparatus component 110 is flexible enough to travel through a tortuous path. During the feeding process, a user typically observes the travel of the catheter apparatus component 110 by x-ray or other technology as the catheter travels through the blood vessel. During the feeding process, the micro-anchor 116 remains inside of the guidewire sheath 114. The catheter apparatus component 110 is fed and guided until it reaches, for example, the superficial temporal artery in the side of a patient's face, or other appropriate artery. The guidewire 112 may then be forced out of an end of the guidewire sheath 114, causing the micro-anchor 116 to exit the guidewire sheath 114 and to deploy. As it is made from a shape memory alloy exhibiting a temperature response at approximately body temperature, the micro-anchor 116 will then deploy to its original shape (i.e., expanded shape) within the superficial temporal artery, or other appropriate artery.

The micro-anchor 116 may be accessible regardless of the rotation of the micro-anchor 116 within the artery or other vessel. The size of the micro-anchor is selected for the artery or vessel. For example, for a superficial temporal artery, the diameter of the deployed or expanded micro-anchor may be any value or range of values between about 1.5 mm to 5 mm. It will be appreciated that the diameter may be less than 1.5 mm or more than 5 mm.

The medical device 100 also has an anchoring device 120 component. The device may include a pin portion 122 and a handle portion 124. Further, the handle portion may take on various forms, such as, but not limited to, the embodiment shown in FIG. 1, wherein the handle portion 124 is circular and is divided into three hollow sections by dividing member 126. The dividing member may be positioned to facilitate use of the anchoring device under a fluoroscope such that the handle portion 124 assists in aligning the pin portion 122 at the desired location. In this manner, the handle portion 124 provides means for aligning the pin portion 122 with the desired target location to intersect with the micro-anchor deployed in the vessel. In other embodiments, the handle portion 124 may be divided into four hollow sections.

The pin portion 122 is inserted substantially perpendicularly to the artery or other vessel in which the micro-anchor is deployed. The pin portion 122 is guided to and through the micro-anchor 116 to stabilize the micro-anchor 116, and, therefore the guidewire 112. The stabilization of the guidewire 112 increases the ease of subsequent medical treatments, such as angioplasty and stenting processes.

Embodiments of the invention are directed to a micro-anchor 116 that ensures better anchoring over prior art solutions. In particular, the micro-anchor 116 is designed and configured to receive the pin portion 122 of the anchoring device 120. The micro-anchor 116 described herein may provide greater control over the manipulation and positioning of a guidewire for the placement of medical devices.

Figure 2A:
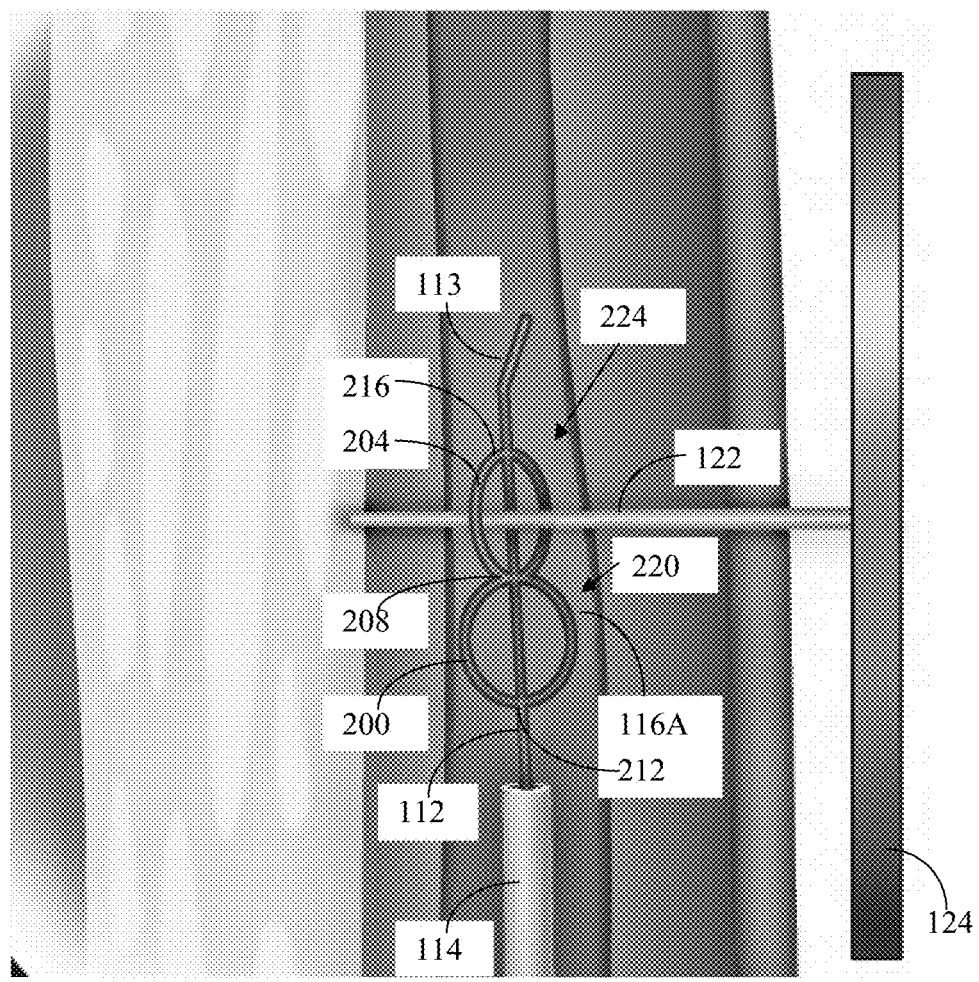
FIG. 2A is a schematic diagram of a micro-anchor according to one embodiment of the invention.

FIG. 2A is an exemplary and non-limiting micro-anchor 116A according to a first embodiment of the invention. The micro-anchor 116A comprises a first ring 200 and a second ring 204, where the second ring is connected to the first ring at connection point 208 to essentially form a figure eight shaped micro-anchor.

In the embodiment shown in FIG. 2A, the rings 200, 204 are the same size. However, in other embodiments, the rings 200, 204 may be different sizes. For example, ring 200 may be smaller than ring 204; in another example, ring 204 may be smaller than ring 200.

In some embodiments, the first ring 200 is oriented at a different angle than the second ring 204. For example, the second ring 204 may be positioned at a 90 degree relative to the first ring 200. It will be appreciated that the angle may be less than or more than 90 degrees. By orienting the rings 200, 204 at different angles, it is more likely that the pin portion 122 of the anchoring device 120 will engage with either ring 200 or ring 204.

While the micro-anchor is shown in FIG. 2 having a figure eight shape, it will be appreciated that additional rings may be used to form the micro-anchor. Each two rings form a figure-eight shape, and the plurality of rings forming a chain like connection of rings. Each of the different rings can be oriented at a different angle to increase the likelihood that the pin portion 122 of the anchoring device 120 will engage with one of the rings. For example, in a micro-anchor having four rings, each ring can be oriented at 45°, 90°, 135° and 180° respectively. It will be appreciated that other angles may be selected to provide for improved engagement of the pin portion 122 and the micro-anchor 116A.

Furthermore, while the rings are shown to be in the shape of a circle, one of ordinary skill in the art will appreciate that other shapes may be used including, without limitation, ellipses and polygons (not shown).

The micro-anchor 116A is connected to the guidewire 112 by connecting either or both the first ring 200 or the second ring 204 to the guidewire 112. The first ring 200 and second ring 204 are co-axial with one another and with the guidewire 112. In the embodiment shown in FIG. 2A, the first ring 200 is co-planar with a longitudinal plane of the guidewire 112, while the second ring 204 is not. It will be appreciated that in alternative embodiments, the second ring 204 may be coplanar with the longitudinal plan of the guidewire 112, while the first ring 200 is not, or that neither of the rings 200, 204 are coplanar with the longitudinal plane of the guidewire 112.

In one embodiment, as shown in FIG. 2A, both rings 200, 204 of the micro-anchor 116A are connected to the guidewire 112 at three different points: connection point 208, connection point 212 and connection point 216. Connection point 212 is located on the first ring 200, connection point 216 is located on the second ring 204, and connection point 208 is at the junction of the first ring 204 and second ring 208. In FIG. 2A, the connection points 212 and 216 are located at opposite ends 220, 224 of the micro-anchor 116A. The connection point 212 is closest to the guidewire sheath 114, and the connection point 216 is farthest from the guidewire sheath 114. The connection may be done by molding, welding, pressing or the like as known to one of skill in the art. It will be appreciated that the connections may occur at other locations than those shown in FIG. 2 and that fewer or more than the number of connections illustrated may be used to attach the micro-anchor 116A to the guidewire 112.

In one embodiment, as shown in FIG. 2A, the guidewire 112 has a short angulated tip 113, the tip 113 being positioned outside the maximum scope of the deployed micro-anchor 116A. In one embodiment, the micro-anchor 116A is located a short distance from the tip. For example, the micro-anchor 116A may be located any distance or range of distances between 2-15 mm from the distal tip. It will be appreciated that the distance may be less than 2 mm or more than 15 mm. Furthermore, it will be appreciated that the tip of the guidewire 112 may be the micro-anchor 116A itself (i.e., the guidewire does not include the angulated tip 113).

As noted above, the guidewire 112 may be composed of stainless steel which may be monofilament or braided. The guidewire 112 and the micro-anchor 116A may instead be composed of a shape-memory alloy, such as nitinol. Alternatively, the shape-memory alloy may be a copper-aluminum-nickel, or a nickel-titanium, and may be created by alloying zinc, copper, gold and iron. Additionally, the guidewire 112 may be coated in Teflon, polyurethane, or another lubricious polymer. As it is made from a shape memory alloy exhibiting a temperature response at approximately body temperature, the micro-anchor 116A will then deploy to its expanded shape within the superficial temporal artery, or other appropriate artery.

It will be appreciated that the micro-anchor 116A having the figure eight shape may be formed by molding the micro-anchor 116A out of a malleable material to have a shape similar to that shown in FIG. 2A. Alternatively, the rings 200, 204 may be formed first by bending a straight material, such as wire, into two separate rings, and then connecting the two rings together at the connection point by, for example, soldering, pressing, welding, etc. In another example, a wire may be etched into the shape shown in FIG. 2A. It will be appreciated that a number of other techniques and processes for making the micro-anchor 116A are contemplated, and the examples provided herein are not limiting.

In use, the micro-anchor 116A is delivered to a patient site as described above in a first, collapsed shape. At the patient site, the micro-anchor 116A is deployed and expanded into its second, expanded shape, shown in FIG. 2A. The micro-anchor 116A expands within the artery or vessel so that the micro-anchor 116A engaged with the inner surface of the artery or vessel; alternatively, the micro-anchor 116A expands within the artery or vessel so that the micro-anchor 116A fills up a substantial portion but does not engage the vessel or artery. As described above, the micro-anchor 116A may be anchored at the patient site using the anchoring device 120. For example, the pin portion 122 of the anchoring device 120 may be guided by the handle portion 124 to go through either one of the first ring 200 or the second ring 204 of the micro-anchor 116A to anchor the guidewire 112.

Figures 2B, 2C:
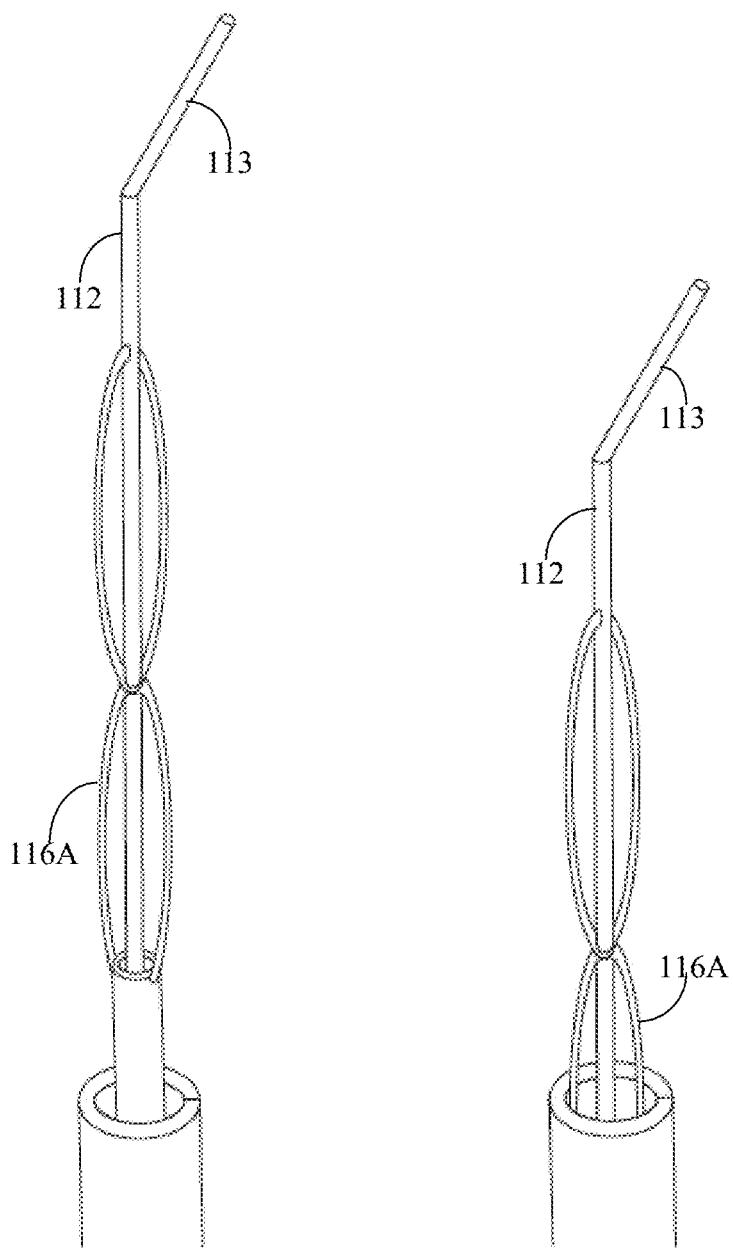
FIG. 2B is a schematic diagram of the micro-anchor of FIG. 2A in a collapsed position prior to entering into the catheter.
FIG. 2C is a schematic diagram of the micro-anchor of FIG. 2A in a collapsed position partially placed into the catheter.

FIG. 2B shows a schematic diagram of the micro-anchor 116A of FIG. 2A in a collapsed position prior to entering into the catheter 114. FIG. 2C shows a schematic diagram of the micro-anchor 116A of FIG. 2A in a collapsed position partially placed into the catheter 114.

Figure 3A:
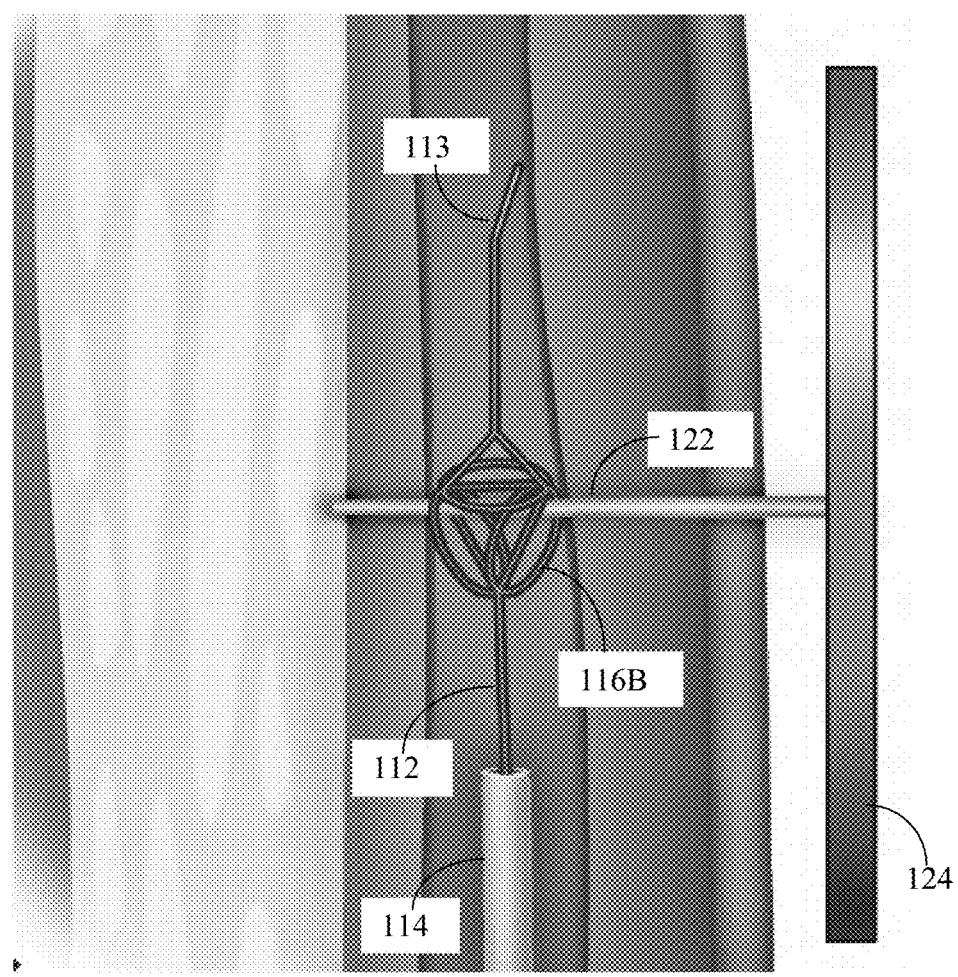
FIG. 3A is a schematic diagram of a micro-anchor according to one embodiment of the invention.
Figure 3B:
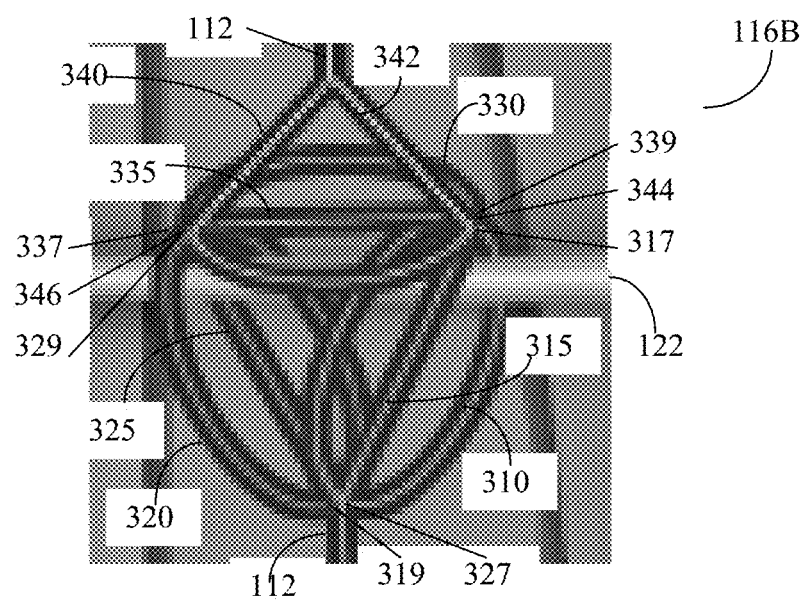
FIG. 3B is a detailed view of the micro-anchor of FIG. 3A.

FIG. 3A is an exemplary and non-limiting micro-anchor 116B according to another embodiment of the invention. FIG. 3B provides an enlarged view of the micro-anchor 116B.

The micro-anchor 116B itself comprises a plurality of rings connect to one another. As shown in detail in FIG. 3B, the micro-anchor 116B includes three rings 310, 320 and 330. Rings 310, 320 and 330 each include a support 315, 325, and 335, respectively. The support 315 passes through an axis of the ring 310 and is connected to ring 310 at connection points 317 and 319, support 325 passes through an axis of the ring 320 and is connected to ring 320 at connection points 327 and 329, and support 325 passes through ring 330 and is connected to ring 330 at 337 and 339.

Ring 310 is connected to ring 320 at connection point 319, ring 320 is connected to ring 330 at connection point 329, and ring 330 is connected to ring 310 at connection point 339. The connection may be done by pressing, soldering, welding or the like. Alternatively, the micro-anchor 116B may be formed by etching a wire.

While in FIG. 3A ring 330 appears closest to the tip 113, one of ordinary skill in the art will appreciate that in alternative embodiments where ring 330 is closest to the sheath 114 is also possible and does not depart from the scope of the invention. Furthermore, while the rings 310, 320, and 330 are shown to be in the shape of a circle, one of ordinary skill in the art will appreciate that other shapes may be used including, without limitation, ellipses and polygons (not shown).

The guidewire 112 is split into a proximal portion and a distal portion. The guidewire 112 is further split at the proximal end of the distal portion to form first guidewire portion 340 and second guidewire portion 342. First guidewire portion 340 is connected to micro-anchor 116B at connection point 344. Second guidewire portion 342 is connected to micro-anchor 116B at connection point 346. It will be appreciated that connections may occur at other places on the micro-anchor 116B than those shown in FIGS. 3A and 3B. Alternatively, the micro-anchor 116B can include guidewire connection elements that are similar to the guidewire portions 340, 342 so that the micro-anchor 116A has the shape shown in FIGS. 3A and 3B, and the guidewire connection elements are each connected to the guidewire at the same location.

The rings 310, 320, 330 are positioned such that when the micro-anchor 116B is expanded, the rings 320, 320, 330 together form the outer surface of the micro-anchor 116B. As shown in FIG. 3B, none of the supports 315, 325, 335 are co-axial with the guidewire 112 or one another, and none of the supports 315, 325, 335 are parallel with another. Additionally, as shown in FIG. 3B, the supports 315, 325, 335 form a generally triangular shape when the micro-anchor is expanded. The positioning of the rings in this manner ensures that regardless of the angle respective of the pin 122 the micro-anchor 116B is positioned, the pin 122 can successfully affix the micro-anchor 116*b* within the vessel.

The micro-anchor 116B is connected to a guidewire 112 on both ends of the micro-anchor 116B. In one embodiment the guidewire 112 has a short angulated tip 113, the tip 113 being positioned outside the maximum scope of the deployed micro-anchor 116B.

The micro-anchor 116B may instead be composed of a shape-memory alloy, such as nitinol. Alternatively, the shape-memory alloy may be a copper-aluminum-nickel, nickel-titanium or the like, and may be created by alloying, for example, zinc, copper, gold, iron, and the like. As the micro-anchor 116B is made from a shape memory alloy exhibiting a temperature response at approximately body temperature, the micro-anchor 116B will then deploy to its original shape within the superficial temporal artery, or other appropriate artery.

In use, the micro-anchor 116B is delivered to a patient site as described above in a first, collapsed shape. At the patient site, the micro-anchor 116B is deployed and expanded into its second, expanded shape, shown in FIGS. 3A and 3B. The micro-anchor 116B expands within the artery or vessel so that the micro-anchor 116B engaged with the inner surface of the artery or vessel; alternatively, the micro-anchor 116B expands within the artery or vessel so that the micro-anchor 116B fills up a substantial portion but does not engage the vessel or artery. As described above, the micro-anchor 116B may be anchored at the patient site using the anchoring device 120. For example, the pin portion 122 of the anchoring device 120 may be guided by the handle portion 124 to go through any of the first ring 310, second ring 320 and/or the space 360 between the third ring 330 and the guidewire 112 of the micro-anchor 116A to anchor the guidewire 112. In FIGS. 3A and 3B, the pin portion 122 of the anchoring device 120 is shown passing through, and, therefore, engaging both the first ring 310 and the second ring 320.

FIG. 3C shows a schematic diagram of the micro-anchor 116B of FIG. 3A in a collapsed position prior to entering into the catheter 114. FIG. 3D shows a schematic diagram of the micro-anchor of 116B of FIG. 3A in a collapsed position partially placed into the catheter 114.

Figure 4:
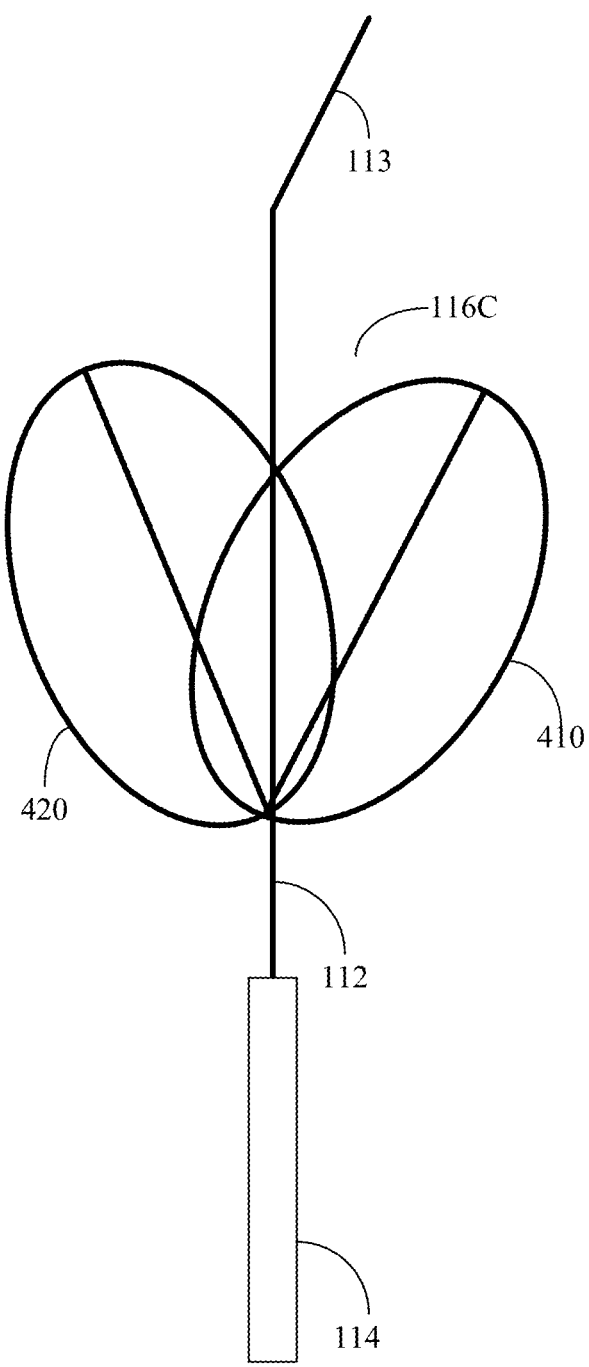
FIG. 4 is a schematic diagram of a micro-anchor according to one embodiment of the invention.

FIG. 4 is an exemplary and non-limiting micro-anchor 116C according to another embodiment of the invention. The micro-anchor 116C includes rings 410 and 420, each having a support 415, 425. Support 415 extends from connection point 417 to connection point 419 of the first ring 410 and support 425 extends from connection point 427 to connection point 429 of the second ring 420. As shown in FIG. 4, the rings 410, 420 are connected together only at connection point 408, and the rings 410, 420 are also only connected to the guidewire 112 at connection point 408 using known techniques. It will be appreciated that in an alternative embodiment, ring 410 may connected to the guidewire at a first connection point and that ring 420 may be connected to the guidewire at a second, different location. In this alternative embodiment, the distance between the two connection points may be selected to ensure a better change of engagement with one of the rings 410, 420.

As shown in FIG. 4, the rings 410 and 420 each extend out at different angles relative to the longitudinal axis of the guidewire 112. As shown in FIG. 4, both rings 410, 420 extend out at about a 30 degree angle relative to the longitudinal axis of the guidewire 112. It will be appreciated that the angle may be any value or range of values between about 5 degrees and 90 degrees, and that the angle may also be less than 5 degrees or more than 90 degrees.

While two rings 410 and 420 are shown, one of ordinary skill in the art would readily appreciate that any number of rings may be used without departing from the scope of the invention. Moreover, while elements 410 and 420 are shown as circles, one of ordinary skill in the art would readily appreciate that other shapes may be used, including without limitations ellipses and polygons.

The micro-anchor 116C may instead be composed of a shape-memory alloy, such as nitinol. Alternatively, the shape-memory alloy may be a copper-aluminum-nickel, nickel-titanium or the like, and may be created by alloying, for example, zinc, copper, gold, iron, and the like.

In use, the micro-anchor 116C is delivered to a patient site as described above in a first, collapsed shape. At the patient site, the micro-anchor 116C is deployed and expanded into its second, expanded shape, shown in FIG. 4. The micro-anchor 116C expands within the artery or vessel so that the micro-anchor 116C engaged with the inner surface of the artery or vessel; alternatively, the micro-anchor 116C expands within the artery or vessel so that the micro-anchor 116C fills up a substantial portion but does not engage the vessel or artery. As described above, the micro-anchor 116C may be anchored at the patient site using the anchoring device 120. For example, the pin portion 122 of the anchoring device 120 may be guided by the handle portion 124 to go through either of the first ring 410 and/or the second ring 420.

Figure 5A:
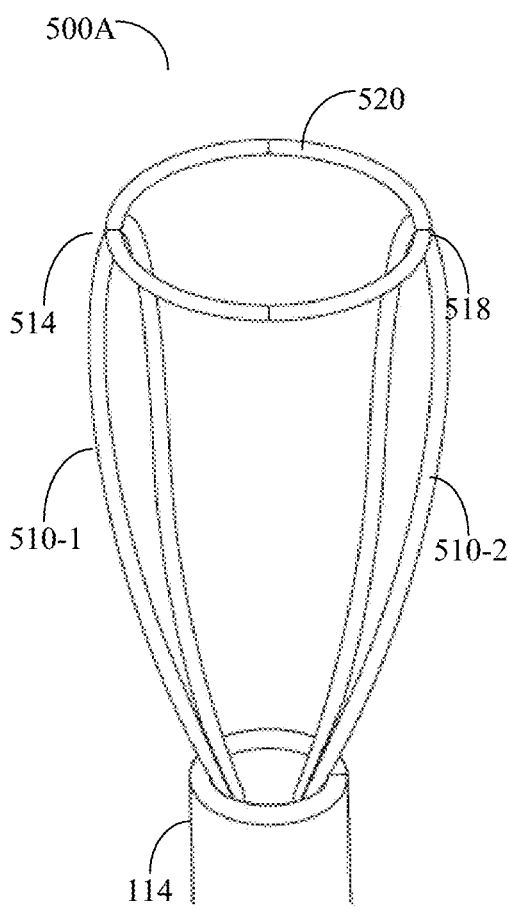
FIG. 5A is a perspective view of a two-petal micro-anchor according to one embodiment of the invention.
Figure 7A:
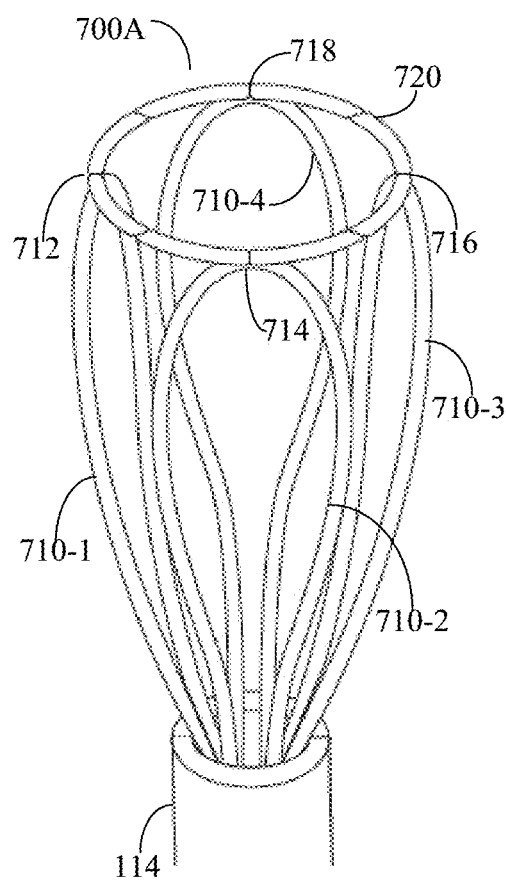
FIG. 7A is a perspective view of a four-petal micro-anchor according to one embodiment of the invention.

Reference is now made to FIGS. 5A, 6A and 7A which depict a two-petal micro-anchor 500A, a three-petal micro-anchor 600A and a four-petal micro-anchor 700A, respectively, each shown in their respective open position. According to the embodiments shown in FIGS. 5A, 6A and 7A, the guidewire 112 placed within the sheath 114 ends with a plurality of petals 510, 610 or 710 which form the micro-anchors 500A, 600A and 700A respectively. As shown, for example, in FIG. 7A, the petals have a generally narrow base near the guidewire sheath 114, and, as the petals extend further away from the guidewire sheath 114, the shape gradually expands into a larger, bulbous section.

The petals may be formed by forming a wire into the shape of the petal and connecting them to the end of the guidewire using known methods. Alternatively, the petals may be formed by etching the end of the guidewire 112 to have the shape shown in FIGS. 5A, 6A and 7A.

In FIG. 5A, the micro-anchor 500A includes two petals 510-1 and 510-2 and a ring 520. The top tip of the petal 510-1 is connected to ring 520 at a first point of contact 514 and the top tip of the petal 510-2 is connected to ring 520 at a second point of contact 518. The connection may be done by pressing, soldering, welding or the like.

Similarly, as shown in FIG. 6A, the micro-anchor 600A includes three petals 610-1, 610-2 and 610-3 and a ring 620. The top tip of the petal 610-1 is connected to ring 620 at a first point of contact 614, the top tip of the petal 510-2 is connected to ring 620 at a second point of contact 618 and the top tip of the petal 510-3 is connected to ring 620 at a third point of contact 612. The connection may be done by pressing, soldering, welding or the like.

Likewise, as shown in FIG. 7A, the micro-anchor 500C includes four petals 710-1, 710-2, 710-3 and 710-4. The top tip of the petal 710-1 is connected to ring 720 at a first point of contact 712, the top tip of the petal 710-2 is connected to ring 720 at a second point of contact 714, the top tip of the petal 710-3 is connected to ring 720 at a third point of contact 716, and the top tip of petal 710-4 is connected to ring 720 at a fourth point of contact 718. The connection may be done by pressing, soldering, welding or the like.

One of ordinary skill in the art will readily appreciate that the combinations shown in FIGS. 5A, 6A and 7A are merely exemplary and additional petals or differently-shaped petals may be implemented without departing from the scope of the invention.

Figure 5B:
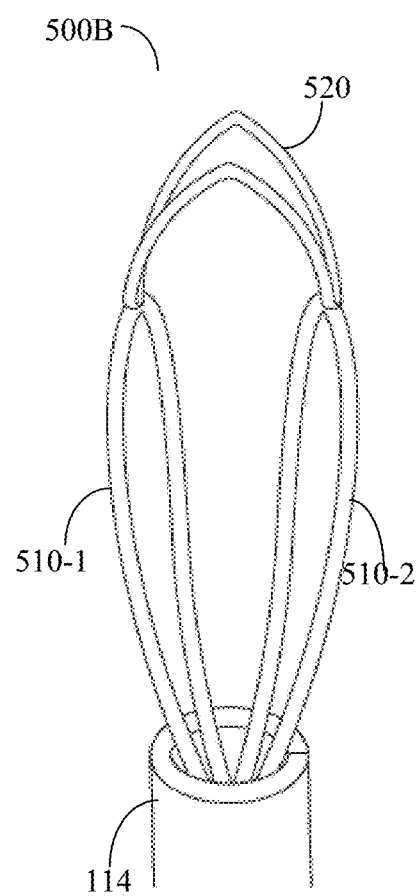
FIG. 5B is a perspective of a the two-petal micro-anchor of FIG. 5A in a collapsed position.
Figure 7B:
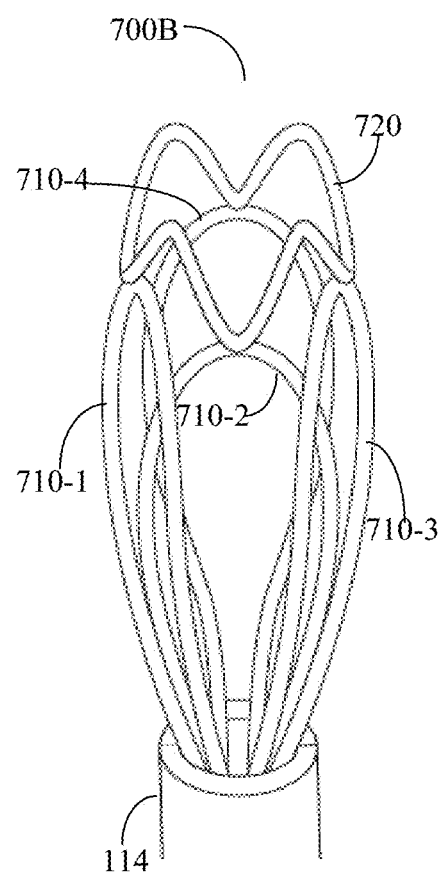
FIG. 7B is a perspective of a the four-petal micro-anchor of FIG. 7A in a collapsed position.

The micro-anchors 500, 600 and 700 are positioned at the end of the guidewire 112 (i.e., the micro-anchor 500, 600 or 700 is the tip of the guidewire 112). The operation of the micro-anchors 500, 600 or 700 is similar to the operation discussed herein in that it is while within the sheath 114 is compressed to fit therein, and, when pushed outside of the sheath 114, it resumes its open position, and may be used for anchoring purposes as described herein. The collapsed positions of the micro-anchors 500, 600, and 700 are shown in FIGS. 5B, 6B and 7B respectively, as collapsed micro-anchors 500B, 600B and 700B respectively.

The micro-anchors 500, 600 or 700 may be composed of a shape-memory alloy, such as nitinol. Alternatively, the shape-memory alloy may be a copper-aluminum-nickel, or a nickel-titanium, and may be created by alloying zinc, copper, gold and iron. As it is made from a shape memory alloy exhibiting a temperature response at approximately body temperature, the micro-anchors 500, 600 or 700 will then deploy to their original shape within the superficial temporal artery, or other appropriate artery.

In an alternative embodiment to that shown in FIGS. 5A, 6A, and 7A, the guidewire 112 may extend through the micro-anchors 500, 600 or 700 and may be further equipped with an angulated tip, such as angulated tip 113 described herein. In such an embodiment, the micro-anchors 500, 600 or 700 would be connected to the guidewire 112 in a manner similar to that previously described herein with reference to FIGS. 2-4.

In use, the micro-anchor 500, 600 or 700 are delivered to a patient site as described above in a first, collapsed shape (500B, 600B or 700B as the case may be). At the patient site, the micro-anchor 500, 600 or 700 is deployed and expanded into its second, expanded shape, shown in FIG. 5A, 6A or 7A, shown as 500B, 600B or 700B respectively. The micro-anchors 500, 600 or 700 expand within the artery or vessel so that the micro-anchors 500, 600 or 700 engage with the inner surface of the artery or vessel; alternatively, the micro-anchors 500, 600 or 700 expand within the artery or vessel so that the micro-anchors 500, 600 or 700 fill up a substantial portion but do not engage the vessel or artery. As described above, the micro-anchors 500, 600 or 700 may be anchored at the patient site using the anchoring device 120. For example, the pin portion 122 of the anchoring device 120 may be guided by the handle portion 124 to go through any one or combination of the petals 510, 610 or 710 of the micro-anchors 500, 600 or 700 respectively or spaces between petals 510, 610 or 710 and the ring 520 to anchor the guidewire 112.

Figure 8:
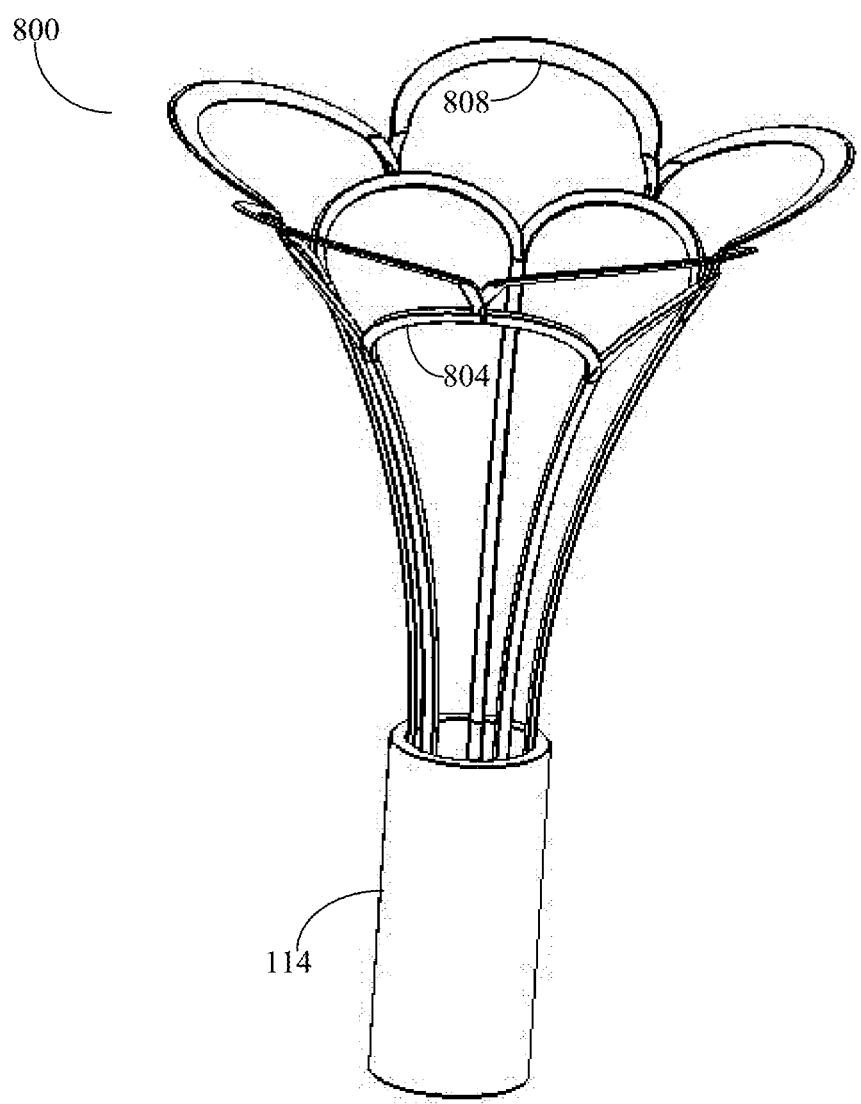
FIG. 8 is schematic diagram of a micro-anchor according to one embodiment of the invention.

Reference is now made to FIG. 8 which depicts an exemplary and non-limiting micro-anchor 800 in accordance with yet another embodiment of the invention. As was discussed with respect of the previous embodiments, micro-anchor 800 may be connected to a guidewire (not shown) that guides the micro-anchor 800 within a sheath 114. In FIG. 8 the micro-anchor is shown in its opened position. When the micro-anchor 800 is in the sheath 114, it is in a collapsed position (not shown). Furthermore, the guidewire may extend beyond the micro-anchor 800 and further have a bent tip as shown with respect to other embodiments detailed herein and which is not repeated yet once again. An anchoring pin may be used to anchor the micro-anchor 800 in ways explained elsewhere herein.

As shown in FIG. 8, the micro-anchor includes a plurality of inner petals 804 and a plurality of outer petals 808. In FIG. 8, the micro-anchor includes five inner petals 804 and five outer petals 808; however, it will be appreciated that the number of inner petals and the number of outer petals may be less than or more than five and that the number of inner petals and the number of outer petals need not be the same.

As shown in FIG. 8, each one of the outer petals 808 is connected to two adjacent inner petals 804. The petals 804, 808 may be connected as shown in FIG. 8 by, for example, pressing, soldering, welding or the like.

The micro-anchor 800 may be composed of a shape-memory alloy, such as nitinol. Alternatively, the shape-memory alloy may be a copper-aluminum-nickel, or a nickel-titanium, and may be created by alloying zinc, copper, gold and iron. As it is made from a shape memory alloy exhibiting a temperature response at approximately body temperature, the micro-anchors 800 will then deploy to their original shape within the superficial temporal artery, or other appropriate artery.

In use, the micro-anchor 800 is delivered to a patient site as described above in a first, collapsed shape (not shown). At the patient site, the micro-anchor 800 is deployed and expanded into its second, expanded shape, shown in FIG. 8. The micro-anchor 800 expands within the artery or vessel so that the micro-anchor 800 engages with the inner surface of the artery or vessel; alternatively, the micro-anchor 800 expands within the artery or vessel so that the micro-anchor 800 fills up a substantial portion but do not engage the vessel or artery. As described above, the micro-anchor 800 may be anchored at the patient site using the anchoring device 120. For example, the pin portion 122 of the anchoring device 120 may be guided by the handle portion 124 to go through any one or combination of the inner petals 804 or outer petals 808 of the micro-anchor 800 respectively.

Figure 9A:
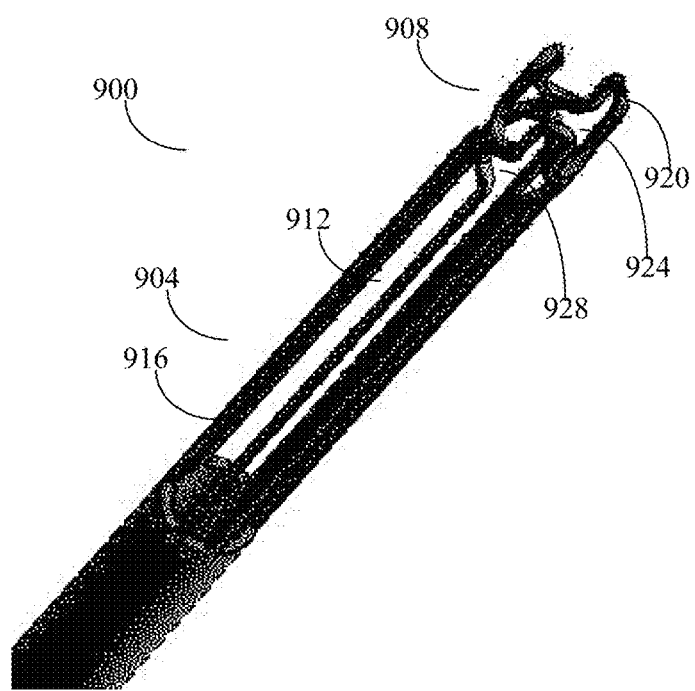
FIG. 9A is a schematic diagram of a non-collapsible micro-anchor according to one embodiment of the invention.
Figure 9B:
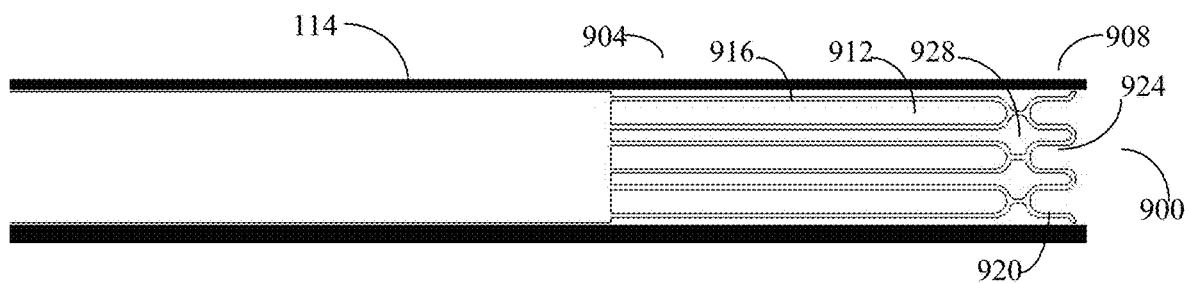
FIG. 9B is a schematic diagram of the non-collapsible micro-anchor in a sheath.

In FIGS. 9A and 9B there is shown another exemplary and non-limiting micro-anchor 900 in accordance with yet another embodiment of the invention. The micro-anchor 900 is shown outside of a sheath 114 in FIG. 9A and within a sheath 114 in FIG. 9B. The micro-anchor 900 differs from its predecessor micro-anchors described herein in that it has only a single mode, that is, the micro-anchor 900 does not expand or collapse. Furthermore, a guidewire may extend beyond the micro-anchor 900 and further have a bent tip as shown with respect to other embodiments detailed herein and which is not repeated yet once again. The micro-anchor 900 includes a proximal end 904 and a distal end 908. The proximal end 904 includes a number of openings 912 defined by structure 916, and the distal end 908 includes a structure 920 connected to the structure 916 that defines a number of additional openings 924. The additional openings 924 are concentric with the openings 912, but also include additional opening portions 928 that extend beyond the length of the openings 912. An anchoring pin may be used to anchor the micro-anchor 900 in ways explained elsewhere herein. The use of micro-anchor 900 is of particular value in cases where it is not desirable or otherwise possible to use an expanding micro-anchor of the micro-anchors described herein which have expanding capabilities.

The micro-anchor 900 may be composed of a shape-memory alloy, such as nitinol. Alternatively, the shape-memory alloy may be a copper-aluminum-nickel, or a nickel-titanium, and may be created by alloying zinc, copper, gold and iron. As it is made from a shape memory alloy exhibiting a temperature response at approximately body temperature, the micro-anchors 900 will then deploy to their original shape within the superficial temporal artery, or other appropriate artery. However, one of ordinary skill in the art would readily appreciate that other metals and/or alloys may be used, including but not limited to non-shape memory alloy.

In another exemplary process of deployment, the presently disclosed system may be used to access and navigate a type III aortic arch. A first catheter, such as a Simmons catheter or other catheter having a reverse curve or hook configuration, may be used to gain access to the ascending aorta and carotid artery and to secure the catheter in place. A micro catheter or guidewire sheath may then be advanced through the first catheter and advanced into the carotid artery. In one embodiment, a guidewire having a micro-anchor of any one of the types disclosed herein, is disposed within the micro catheter. The micro-anchor has a tip that may be angled to facilitate selection of the external carotid artery and navigate the micro catheter to the desired location. This would allow anchoring the system to enable accurate and undisturbed access to the internal carotid artery, thereby facilitating the stenting procedure therein. One of ordinary skill in the art would readily appreciate that the system can be similarly used in cases of other arteries where the securing of such or a similar system is necessary, without departing from the scope of the invention. Upon reaching the desired location, the micro-anchor may be extended from the micro catheter allowing the micro-anchor to expand and be secured in the vessel with an anchoring device as discussed below. In another embodiment, a conventional guidewire may be used to advance the micro catheter to the desired location. Upon reaching the desired location, the conventional guidewire may be removed, and the guidewire having micro-anchor may be inserted and advanced through the catheter until the micro-anchor extends from the micro catheter and expands to be secured in the vessel. Once the micro-anchor is secured, a carotid stenting or other procedure may be performed. In this manner the system may provide a stabilized platform for intervention in tortuous arteries of the head, neck or other extremities.

The intravascular anchor described herein facilitates the stenting of the internal carotid artery or common carotid artery. However, this should not be viewed as limiting the scope of the invention. For instance, and without limitations, the disclosed inventions as well as embodiments thereof, may apply to the stenting of the subclavian artery by anchoring in the radial artery. It may be further used, without limitation, for stenting in the lower extremity in situations of acute angulation or tortuosity at the aorto iliac bifurcation. In this case, a practitioner could access the common femoral artery using a retrograde contralateral approach and intervene in the opposite lower extremity by anchoring a device implemented according to the principles of the invention anywhere in the lower extremity.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention has been described in relation to particular examples, which are intended in all respects to be illustrative rather than restrictive. Those skilled in the art will appreciate that many different combinations will be suitable for practicing the present invention. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. An intravascular system comprising:
a guidewire;
a micro-anchor connected to the guidewire, the micro-anchor comprising:
   a first ring connected to the guidewire; and,
   a second ring connected to the first ring and the guidewire,
   wherein the micro-anchor is configured to transition from within a sheath catheter to a deployed state outside the sheath catheter when the micro-anchor is delivered to a first location in a peripheral artery; and
an external device having a pin and a handle, wherein the pin is fixed perpendicular to the handle,
wherein the pin is configured to be inserted, using the handle, from a second location outside of a body of a patient, through skin of the patient, and through a side wall of the peripheral artery, at a third location, into the peripheral artery to engage the deployed micro-anchor,
wherein the second location is aligned with the micro-anchor in the deployed state in the first location,
wherein the pin is further configured to pass through the side wall of the peripheral artery at a fourth location, opposite the third location, to secure the micro-anchor in the peripheral artery at the first location and provide an end-to-end stabilization to the guidewire.

2. The intravascular system of claim 1, wherein the first ring is at an angle relative to the second ring enabling engagement with the pin inserted from outside of the body of the patient.

3. The intravascular system of claim 1, further comprising a third ring, wherein the third ring is connected to at least one of the first ring, the second ring and the guidewire.

4. The intravascular system of claim 1, wherein the first ring comprises a first support extending from one end of the first ring to an opposite end of the first ring, and
   wherein the second ring comprises a second support extending from one end of the second ring to an opposite end of the second ring.

5. The intravascular system of claim 4, wherein the first support is coaxial with the second support of the second ring.

6. The intravascular system of claim 5, wherein the first support and the second support are further coaxial with a longitudinal axis of the guidewire.

7. The intravascular system of claim 1, wherein the pin is configured to be inserted through at least one of the first ring and the second ring to secure the guidewire within the peripheral artery.

8. The intravascular system of claim 1, wherein the guidewire comprises a tip, wherein the tip of the guidewire is angled to facilitate selection of an external carotid artery and navigate the guidewire therein.

9. The intravascular system of claim 1, wherein the micro-anchor is in a first collapsed state when the micro-anchor is within the sheath catheter.

10. The intravascular system of claim 9, wherein when the micro-anchor is in the deployed state outside the sheath catheter the micro-anchor is expanded relative to the first collapsed state.

11. The intravascular system of claim 1, wherein the micro-anchor is attached to a location at a tip of the guidewire.

12. An intravascular system comprising:
a guidewire; and
a micro-anchor connected to the guidewire, the micro-anchor comprising:
   a plurality of petals connected to the guidewire; and
   a ring connected to each of the plurality of petals,
   wherein the micro-anchor is configured to transition from within a sheath catheter to outside of the sheath catheter and deploy to an expanded state when the micro-anchor is at a first location in a peripheral artery of a patient,
   wherein the micro-anchor is capable of receiving a pin fixed perpendicular to a handle,
   wherein the pin is configured to be inserted, using the handle, from a second location outside of a body of the patient through a skin of the patient, through a side wall of the peripheral artery, at a third location, into the peripheral artery, to engage the micro-anchor at the first location, and out of the peripheral artery through the sidewall of the peripheral artery at a fourth location,
   wherein the pin is configured to be inserted through at least one of the plurality of petals of micro-anchor to engage the micro-anchor,
   wherein the second location is aligned with the micro-anchor in the expanded state,
   wherein the pin is further configured to anchor to secure the guidewire at the first location within the peripheral artery of the patient.

13. The intravascular system of claim 12, wherein the guidewire extends through the micro-anchor.

14. The intravascular system of claim 12,
wherein in the expanded state, the micro-anchor is expanded relative to a collapsed state and the micro-anchor is configured to be anchored within the peripheral artery using the pin from outside of the body of the patient,
wherein when the micro-anchor is in the expanded state the micro-anchor is expanded relative to the collapsed state.

15. An intravascular system comprising:
a guidewire;
a micro-anchor connected to the guidewire, wherein the micro-anchor is configured to transition from a collapsed state, within a sheath catheter, to an expanded state, outside of the sheath catheter; and
an external device comprising a pin and a handle, wherein the pin is fixed to the handle, and wherein the pin is configured to be aligned with a location of the micro-anchor within a peripheral artery of a patient, and
wherein the pin is configured to be guided from outside a body of the patient and through a skin of the patient, using the handle, to engage the micro-anchor in the expanded state, outside of the sheath catheter to anchor and secure the guidewire within the peripheral artery of the patient.

16. The intravascular system of claim 15, wherein the guidewire comprises a tip, wherein the tip of the guidewire is angled to facilitate selection of an external carotid artery and navigate the guidewire therein.

17. A method for anchoring and securing a guidewire to provide a manipulation capability and stabilization to a procedural catheter during a minimally invasive procedure, the method comprising:
making an incision at an entry site into a superficial artery of a patient, for the procedural catheter, the procedural catheter including a guidewire sheath with an enclosed guidewire and a micro-anchor;

inserting the procedural catheter into the superficial artery, wherein the micro-anchor is in a collapsed state when the procedural catheter during the inserting;

guiding the procedural catheter to a target location within the superficial artery;

causing the micro-anchor to exit the sheath and deploy at the target location within the superficial artery using the guidewire;

aligning an anchoring device with the micro-anchor at the target location and outside skin of the patient, the anchoring device including a handle and a pin fixed rigidly to the handle, wherein the micro-anchor is in a deployed state at the target location; and inserting the pin of the anchoring device through the skin of the patient to intersect with the micro-anchor and secure the micro-anchor in place within the superficial artery;

fixing the guidewire in place within the superficial artery of the patient to provide stability and manipulation capability for the minimally invasive procedure.

\* \* \* \* \*